(12) United States Patent
Yamakawa et al.

(10) Patent No.: US 8,747,744 B2
(45) Date of Patent: Jun. 10, 2014

(54) CHEMICAL ANALYZER

(71) Applicant: Hitachi High-Technologies Corporation, Tokyo (JP)

(72) Inventors: Hironobu Yamakawa, Tokyo (JP); Yoichi Aruga, Mito (JP); Takenori Okusa, Mito (JP); Taisaku Seino, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/738,555

(22) Filed: Jan. 10, 2013

(65) Prior Publication Data

US 2013/0121883 A1    May 16, 2013

Related U.S. Application Data

(62) Division of application No. 13/201,491, filed as application No. PCT/JP2010/001114 on Feb. 22, 2010.

(30) Foreign Application Priority Data

Feb. 27, 2009  (JP) ................ 2009-045030
Feb. 27, 2009  (JP) ................ 2009-045031

(51) Int. Cl.
| | |
|---|---|
| *G01N 33/50* | (2006.01) |
| *B01F 13/02* | (2006.01) |
| *G01N 35/02* | (2006.01) |
| *G01L 9/00* | (2006.01) |
| *G01N 35/00* | (2006.01) |
| *G01N 35/04* | (2006.01) |

(52) U.S. Cl.
CPC .......... *B01F 13/0272* (2013.01); *G01N 35/025* (2013.01); *G01N 2035/00544* (2013.01); *G01N 2035/0437* (2013.01); *G01L 9/00* (2013.01); *G01L 9/0041* (2013.01)
USPC ........................................ 422/64; 422/82.13

(58) Field of Classification Search
CPC ...... B01F 13/0272; G01N 35/025; G01L 9/00
See application file for complete search history.

(56) References Cited

U.S. PATENT DOCUMENTS

| | | | |
|---|---|---|---|
| 2002/0152954 A1* | 10/2002 | Takamori et al. ............ | 118/52 |
| 2003/0032191 A1* | 2/2003 | Hilson et al. ................ | 436/47 |
| 2007/0018344 A1 | 1/2007 | Mueller et al. | |

FOREIGN PATENT DOCUMENTS

| | | |
|---|---|---|
| JP | 62-32332 A | 2/1987 |
| JP | 63-68399 A | 3/1988 |
| JP | 4-210812 A | 7/1992 |

(Continued)

*Primary Examiner* — P. Kathryn Wright
(74) *Attorney, Agent, or Firm* — Mattingly & Malur, PC

(57) ABSTRACT

An automatic chemical analyzer in which a reaction solution is stirred by air ejected from an air ejection hole placed above a reaction container. The reaction region can be washed and cleaned sufficiently without causing damage, such as exfoliation of a coating reagent. A reaction container disk is provided with a pore and a pressure detector connected with the pore. Before and after the stirring operation, the ejection hole (nozzle) ejecting air is moved and the output value of the pressure detector is compared with a previously measured normal value. With a discharge pipe and a suction pipe inserted to the opening of the reaction container to be close to both ends of the opening and the side wall of the container, the reaction region at the bottom of the container is washed by continuous discharge and suction of cleaning fluid.

3 Claims, 12 Drawing Sheets

(56) References Cited

FOREIGN PATENT DOCUMENTS

| | | |
|---|---|---|
| JP | 4-356316 A | 12/1992 |
| JP | 6-39266 A | 2/1994 |
| JP | 7-83939 A | 3/1995 |
| JP | 2004-340791 A | 12/2004 |
| JP | 2007-51863 A | 3/2007 |

\* cited by examiner (A)

(B)

(C)

(A)　　　　　　　　(B)

(A) CENTRAL CROSS-SECTIONAL VIEW (B) BOTTOM VIEW

CHEMICAL ANALYZER

This application is a divisional of U.S. patent application Ser. No. 13/201,491, filed Aug. 15, 2011.

TECHNICAL FIELD

The present invention relates to a chemical analyzer suitable for analysis of trace substances contained in a living organism.

BACKGROUND ART

An automatic analyzer for qualitative/quantitative analyses of biological samples (blood, urine, etc.) performs such an analysis that the color of reaction solution is changed due to reaction of a reagent with analysis-target constituents in a sample (colorimetric analysis). Such an automatic analyzer also performs such an analysis that markers are added directly or indirectly to substances that react specifically with the analysis-target constituents and the number of the markers is counted (immunity analysis), etc. In the automatic analyzer described above, stirring the mixed solution after mixing of the sample and the reagent is effective for promoting the reaction. For reaction between a liquid sample and a liquid reagent, the stirring of the reaction solution is conducted generally by use of a stir bar or the like inserted into the reaction container. However, the use of the stir bar can become impossible when the amount of the reaction solution is small. A technique for stirring reaction solution in a reaction container by use of air ejected from a nozzle is described in Patent Literatures 1 and 2.

After the reaction is completed, suction of the reaction solution is carried out to remove the unreacted surplus sample from the reaction container. Thereafter, in order to enhance the sample removing effect, the reaction container is washed with a cleaning fluid as needed.

Such an analyzer is described in Patent Literature 3, for example.

PRIOR ART LITERATURE

Patent Literature

Patent Literature 1: JP-2007-51863-A
Patent Literature 2: JP-6-39266-A
Patent Literature 3: JP-7-83939-A

SUMMARY OF THE INVENTION

Problem to be Solved by the Invention

In the stirring by use of a stir bar, whether the reaction solution is being stirred successfully or not can be checked with ease since the stir bar is immersed in the reaction solution and rotates in the reaction solution during the stirring operation. In contrast, when the mechanism for stirring the reaction solution with ejected air is used, it is difficult to check whether or not the stirring is being conducted as expected. Even when there is an abnormality in a measurement value obtained by the analysis, it is difficult to judge whether there was an abnormality in the sample or insufficient stirring of the reaction solution led to the abnormal result.

It is therefore an object of the present invention to provide a chemical analyzer having a mechanism for stirring a reaction solution by ejecting air from an air ejection hole and achieving high reliability of analysis result by making it possible to check whether the stirring mechanism is operating normally.

Further, in an analyzer using the aforementioned reaction container, removing the unreacted surplus sample from the reaction container sufficiently is essential for high-accuracy analysis. However, if the supply of the cleaning fluid to the reaction container or the suction of fluid from the reaction container is conducted at a high flow velocity to remove the surplus sample, there is the danger of exfoliation of a coating reagent from the reaction container coated with the reagent. Even though the analyzer described in the Patent Literature 3 carries out the supply of the cleaning fluid or the suction of fluid by inserting a discharge pipe and a suction pipe to the reaction container, the above problem had not been recognized yet.

It is therefore another object of the present invention to provide a chemical analyzer capable of achieving high analysis accuracy and high device reliability by sufficiently washing and cleaning the reaction container without causing any problem (e.g., exfoliation of the coating reagent on the bottom of the reaction container in cases where the reaction container is in a flat dish-like shape).

Means for Solving the Problem

A chemical analyzer in accordance with the present invention for resolving the above problems is configured as follows:

A chemical analyzer comprising: a reaction container setting table on which a plurality of reaction containers each having an opening are set; and an air ejection hole for ejecting air to the opening of the reaction container, wherein at least one selected from a pressure sensor, a temperature sensor and a humidity sensor is provided at a position between reaction container setting positions on the reaction container setting table.

Preferably, the reaction container setting table is provided with a pore and a pressure sensor connected with the pore. Before or after the stirring operation, the ejection hole ejecting air is stopped or moved over the pore, the output value of the sensor at the time of the stoppage/movement of the ejection hole is monitored, and the output value is compared with a previously acquired signal value in a normal state.

Another chemical analyzer in accordance with the present invention is configured as follows:

A chemical analyzer comprising: a reaction container having an opening and a reaction region situated at the center of the reaction container's bottom; a cleaning fluid discharge pipe for discharging cleaning fluid to the reaction container; and a suction pipe for sucking fluid out of the reaction container, wherein the chemical analyzer comprises a control mechanism which controls washing of the reaction container so that: the suction pipe is lowered to the opening of the reaction container prior to the discharge pipe and starts the suction of fluid, and the discharge pipe is subsequently lowered to the opening of the reaction container and discharges the cleaning fluid, and the suction of fluid and the discharge of the cleaning fluid are conducted concurrently for at least a prescribed time period.

Effect of the Invention

In a chemical analyzer having a mechanism for stirring a reaction solution by ejecting air from an air ejection hole, the check on whether the stirring mechanism is operating normally is made possible. Consequently, a chemical analyzer with high reliability of analysis result can be provided.

Another effect of the present invention is as follows:

A chemical analyzer with high analysis accuracy and high device reliability can be provided.

BRIEF DESCRIPTION OF THE DRAWINGS

FIG. 18 is a schematic diagram for explaining the reaction container, the cleaning fluid discharge pipe, the suction pipe, a rinse chip and the cleaning fluid flow in the washing operation in an embodiment of the present invention, wherein FIG. 18(A) is a central cross-sectional view and FIG. 18(B) is a bottom view of the reaction container.

FIG. 20 is a schematic diagram showing another embodiment of the present invention, wherein FIG. 20(A) is a cross-sectional view and FIG. 20(B) is a bottom view of the reaction container.

MODE FOR CARRYING OUT THE INVENTION

Figure 1:
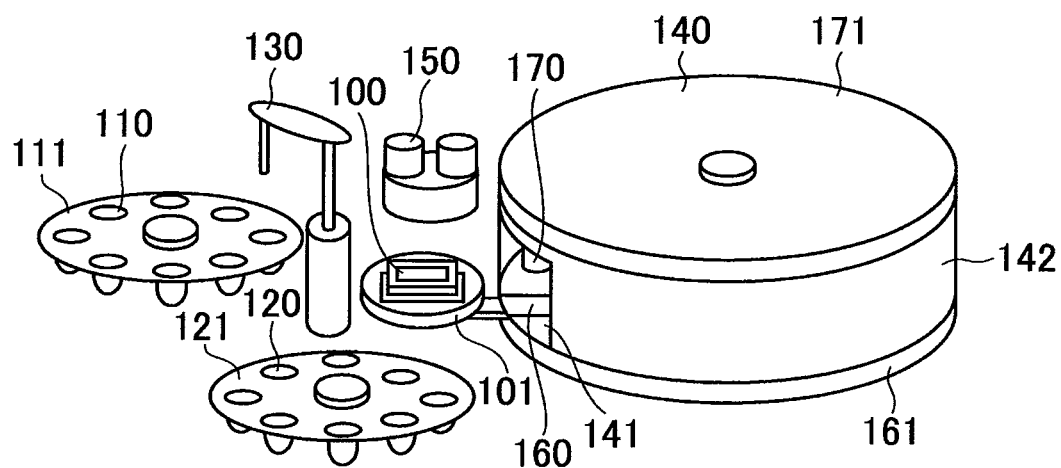
FIG. 1 is an overall schematic diagram of a chemical analyzer in accordance with an embodiment of the present invention.

Referring now to the drawings, a description will be given in detail of preferred embodiments in accordance with the present invention.

First Embodiment

Figure 2:
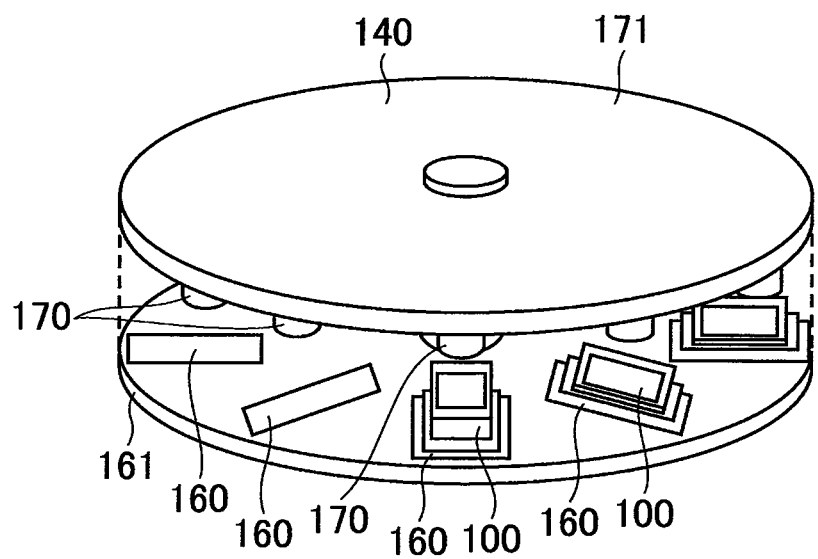
FIG. 2 is a schematic diagram of an incubator unit in the embodiment of the present invention.
Figure 3:
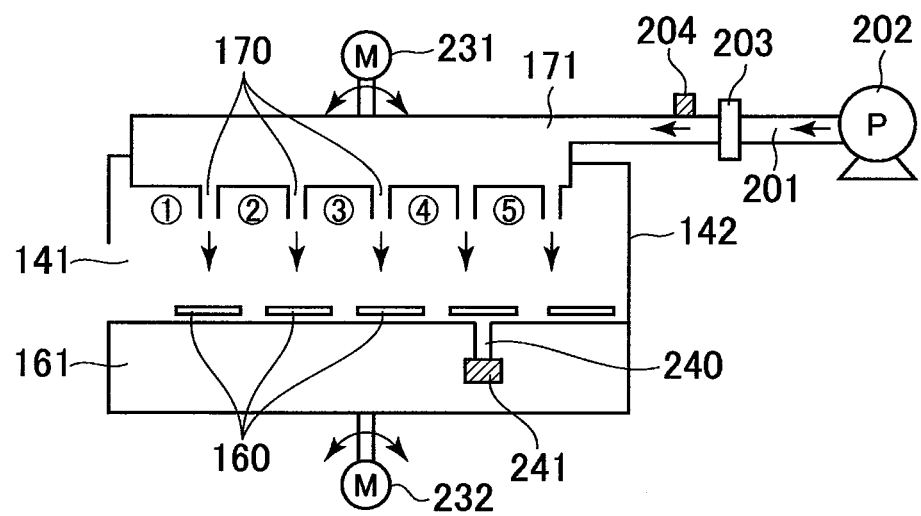
FIG. 3 is a schematic diagram of the incubator unit in the embodiment of the present invention.

First, referring to FIGS. 1 to 3, the configuration of a chemical analyzer in accordance with a first embodiment of the present invention will be described. FIG. 1 is an overall schematic diagram of the chemical analyzer. FIG. 2 is a schematic perspective view showing the inside of an incubator unit. FIG. 3 is an explanatory drawing schematically showing the setup inside the incubator unit viewed from the side.

As shown in FIG. 1, the chemical analyzer comprises a carrier 101 for carrying a small-sized reaction container 100, a sample disk 111 for storing sample containers 110, a reagent disk 121 for storing reagent containers 120, a separate pouring mechanism 130 for pouring a sample and a reagent separately from their respective containers to the reaction container 100, an incubator unit 140 for stirring a reaction solution made up of the sample and the reagent, and an optical detection mechanism 150 including an excitation light irradiator and a fluorescence emission intensity detector. The incubator unit 140 includes a reaction disk 161 having reaction container setting spots 160 on which the reaction containers 100 can be set, a nozzle disk 171 having nozzles 170 for ejecting compressed air, and a side wall 142 surrounding the incubator unit.

As shown in FIG. 2, the nozzle disk 171 and the reaction disk 161 of the incubator unit 140 are components in disk-like shapes. The plurality of nozzles 170 are provided along the circumference of the nozzle disk 171, while the plurality of reaction container setting spots 160 are provided along the circumference of the reaction disk 161. The nozzles 170 and the reaction container setting spots 160 are situated at positions corresponding to each other in the vertical direction, respectively. Each reaction container 100 is placed under one of the nozzles 170. The sample and the reagent in the reaction container 100 are stirred and mixed together by the compressed air ejected from the nozzle 170.

As shown in FIG. 3, the nozzle disk 171 and the reaction disk 161 are driven by drive motors 231 and 232, respectively. The nozzle disk 171 is supplied with the compressed air from an air pump 202 via a filter 203 for removing dust. A pipe pressure sensor 204 is attached to the wall of a pipe 201. One of the reaction container setting spots 160 of the reaction disk 161 is provided with pores 240. A pressure sensor 241 of the diaphragm type (as pressure detecting means) is embedded in a part of the reaction disk 161 at the end of each pore 240.

These components automatically conduct an analysis with prescribed timing as explained below based on previously inputted analysis item information. First, the sample and the reagent are poured from separate containers to a reaction container 100 by the separate pouring mechanism 130. Subsequently, the reaction container 100 is carried from an incubator unit opening 141 to the inside of the incubator by moving the carrier 101 while rotating the reaction disk 161. The reaction container 100 is set on a prescribed reaction container setting spot of the reaction disk 161 and the compressed air is ejected from the nozzle 170 placed over the reaction container. The ejected compressed air collides with the surface of the reaction solution made up of the sample and the reagent and thereby causes a stirring flow in the reaction solution, by which the sample and the reagent are stirred and mixed together. The reaction container 100 after completion of the stirring is taken out from the incubator unit 140 and moved to a position under the detection mechanism 150 by the carrier 101. At this position, optical detection is conducted to the reaction solution in the reaction container 100.

Before and after this analysis operation, the so-called "initialization", including a check on whether each mechanism of the chemical analyzer operates normally or not and an operation for returning each mechanism to its original position, is carried out. In the initialization, a nozzle abnormality detecting operation, for ensuring normal operation of the stirring mechanism, is conducted. In the nozzle abnormality detecting operation, the reaction container setting spots 160 are empty as shown in FIG. 3. The nozzles shown in FIG. 3 are numbered from #1 to #5, for example.

Figure 4:
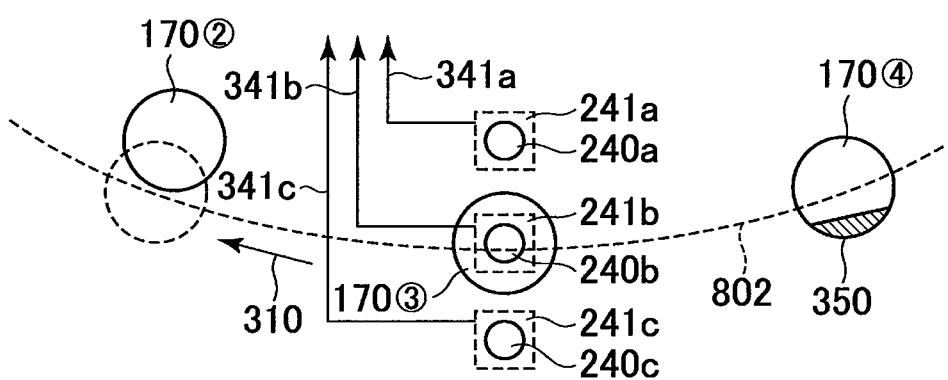
FIG. 4 is a schematic diagram showing the arrangement of nozzles and pores in the embodiment of the present invention.

FIG. 4 is a schematic diagram showing the positions of the nozzles projected onto the reaction disk for explaining the movement of the nozzles and the positional relationship among the nozzles, the pore, etc. In this embodiment, three pores 240a, 240b and 240c are arranged in a line orthogonal to the rotation direction 310 of the nozzles. The dotted line 802 indicates a circumference on the nozzle disk 171 on which the nozzles 170 are provided. Static pressure sensors 241a, 241b and 241c are connected to the pores and output signals 341a, 341b and 341c, respectively. The pore 240b is placed at the central position regarding the nozzle movement 310 and the pores 240a and 240c are placed the same distances apart from the central position. In FIG. 4, positions 170(2), 170(3) and 170(4) of nozzles #2, #3 and #4, among the many nozzles 170, are indicated. FIG. 4 shows a situation in which the nozzle #2 has shifted from its normal position and dust 350 has adhered to the nozzle #4 as will be explained below.

Figure 5:
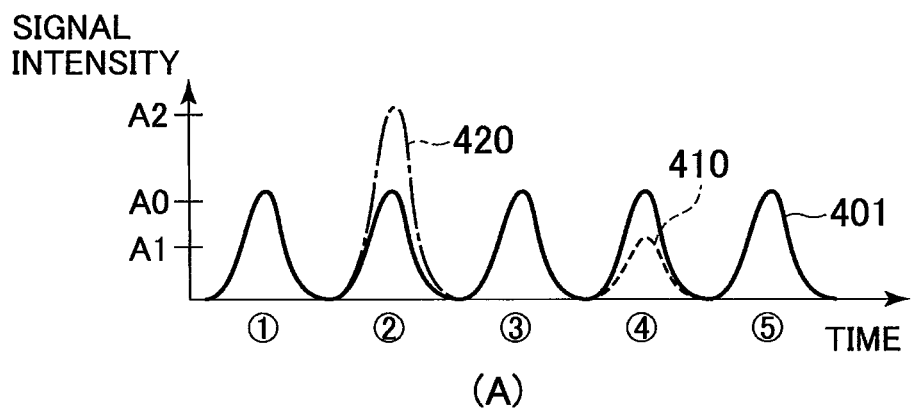
FIG. 5(A) shows an example of an output of one pressure detecting means in the embodiment of the present invention.
FIG. 5(B) shows an example of an output of another pressure sensor detecting means in the embodiment of the present invention.
FIG. 5(C) shows an example of an output of another pressure sensor detecting means in the embodiment of the present invention.
Figure 5:
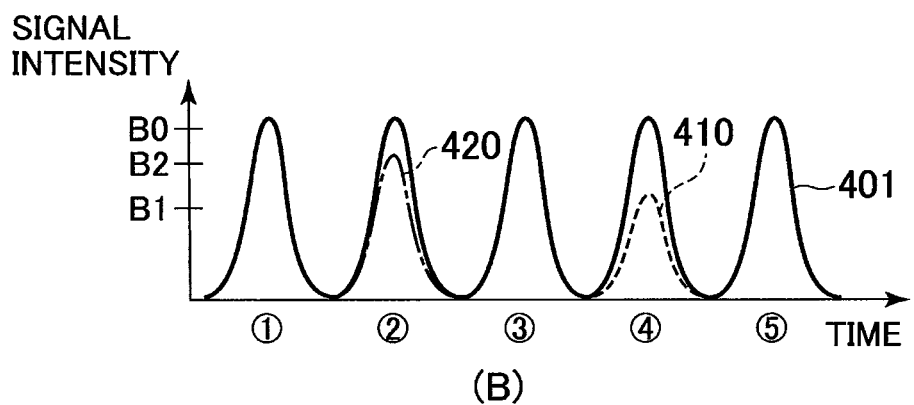
Figure 5:
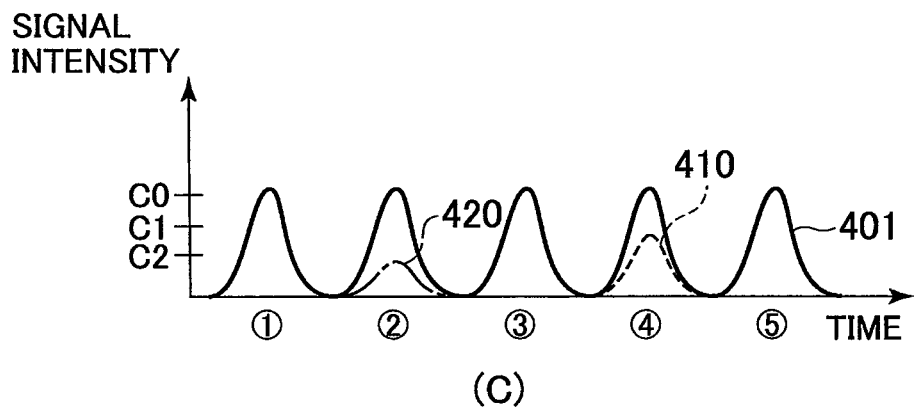

FIG. 5 shows an example of the outputs of the pressure sensors, wherein the horizontal axis of each graph represents time and the vertical axis of each graph represents signal intensity of the output of each pressure sensor. (A), (B) and (C) of FIG. 5 indicate outputs 341a, 341b and 341c of the three pressure sensors shown in FIG. 4, respectively. The compressed air ejected from the nozzle 170 forms a colliding jet flow over the reaction disk 161. Due to the nature of the colliding jet flow, the pressure on the reaction disk (as the collision surface) is the highest at the position right under the nozzle and decreases with the increase in the distance from the nozzle. Thus, if the nozzle disk 171 is moved while continuing the ejection of the compressed air from the nozzle 170, the pressure displays periodic variations corresponding to the nozzles #1-#5 since the pressure reaches a maximum when a nozzle 170 passes right above the pore 240, thereafter decreases, and increases again when the next nozzle passes over the pore 240. The output 341b of the sensor 241b (connected to the pore 240b formed right under the track of the nozzles) is the highest among the outputs of the three sensors. The outputs 341a and 341c are lower than the output 341b and equivalent to each other due to the symmetry. When the stirring mechanism is in its normal state, the output of each pressure sensor takes on the same value for all the nozzles as indicated by the solid line 401 in FIG. 5.

The maximum values of the outputs are A0, B0 and C0, respectively. These values will hereinafter be referred to as "normal values".

First, an example of nozzle abnormality will be explained, in which the nozzles #1, #2, #3 and #5 are in their normal states but the nozzle #4 has turned to a clogged nozzle 170(4) due to the dust 350 adhering thereto as shown in FIG. 4. The dust 350 in the nozzle #4 has formed as a secular variation due to accumulation of dust (particles) smaller than the mesh size of the filter 203. The output value of each sensor in this case is indicated with a dotted line 410 in FIG. 5. All the outputs 341a, 341b and 341c drop at time corresponding to the nozzle #4, the maximum values of the outputs 341a, 341b and 341c corresponding to the nozzle #4 are A1, B1 and C1, respectively. The output profiles also become blunt. The output values regarding the other nozzles of the nozzle disk have not changed substantially from the solid lines. The occurrence of an abnormality (clogging) to the nozzle #4 can be found as above from such output values different from the normal values.

Next, another example of nozzle abnormality will be explained, in which the nozzles #1, #3, #4 and #5 are in their normal states but the position of the nozzle #2 has shifted as indicated with the reference character 170(2) in FIG. 4. The output value of each sensor in this case is indicated with a chain line 420 in FIG. 5. The parts (periods) of the output values 341a, 341b and 341c corresponding to the passage of the nozzles #1, #3, #4 and #5 remain on the solid lines 401 (normal values). However, due to the shift of the nozzle #2 toward the sensor 241a indicated with the reference character 170(2) in FIG. 4, maximum values A2, B2 and C2 of the output values 341a, 341b and 341c corresponding to the nozzle #2 satisfy the relationship A2>B2>C2. The occurrence of the displacement (misalignment) of the nozzle #2 can be found as above from such output values different from the normal values. Such displacement detection works in the same way not only in cases where the position of a single nozzle has shifted but also in cases where the position of the reaction disk or the nozzle disk has shifted.

When the result described above is obtained by the pressure measurement before or after a stirring operation, the analysis using the nozzle #2 or #4 is considered to be under the influence of stirring conditions different from those of the other nozzles, and thus the reliability of the analysis result using the nozzle #2 or #4 is low. Therefore, the device operation program (analyzer operation program) is modified so as not to use the nozzles #2 and #4 from the next analysis. It is possible to previously determine the lowest permissible pressure (greatest permissible pressure change) capable of avoiding substantial deterioration in the stirring performance as performance data of the analyzer, store the lowest permissible pressure in the analyzer's program as a normal value, and compare the output value with the stored normal value. The normal value may be stored as a continuous profile with a high sampling frequency, or it is also possible to output a signal with a low sampling frequency in sync with the nozzle disk driving frequency and use a discrete value (maximum value, minimum value, etc.) of the signal as the normal value. An analysis result obtained by using an abnormal nozzle for the stirring operation may be indicated on the user interface so as to let the user request the supplier of the device (analyzer) to perform the maintenance. It is also possible to provide an LED lamp nearby each nozzle and light the LED lamp when an abnormality has occurred to the nozzle. This realizes high maintainability since the personnel performing the check and maintenance has only to check and clean the abnormal nozzle while disregarding the other nozzles.

As shown in the pressure sensor output examples of FIG. 5, the peaks, etc. of the output value of each pressure sensor are detected at prescribed times if the stirring mechanism is operating normally. If the times of the peaks, etc. have deviated from the prescribed times, there is a possibility of an abnormality in the drive motor 231 for rotating the nozzle disk 171. In such cases, maintenance of the drive motor 231 is desired to be performed.

While the abnormality detecting operation described above may be performed before and after each analysis, the abnormality detecting operation may be performed only at the startup and shutdown of the device (analyzer), or only when the pipe pressure sensor 204 indicated an abnormal value.

While the pores 240 are provided in only one reaction container setting spot 160 in this embodiment in consideration of the restriction on the device space, detection of pressure leaking out during the stirring operation becomes possible if the pores 240 are provided in the spaces between the reaction container setting spots 160. Further, while the three pores 240 and the three sensors 241 are provided at one reaction container setting spot 160 in this embodiment, the detection of a nozzle abnormality based on a change in the sensor output value is possible even with only one pair of pore 240 and sensor 241. It is also possible to provide every reaction container setting spot 160 with the pores 240 and the sensors 241, which is desirable since the need of moving the nozzle disk 171 for the abnormality detecting operation is eliminated.

Furthermore, while the pressure detection is carried out by rotating the nozzle disk 171 in this embodiment, equivalent effects can be achieved also by rotating the reaction disk 161.

Second Embodiment

Figure 6:
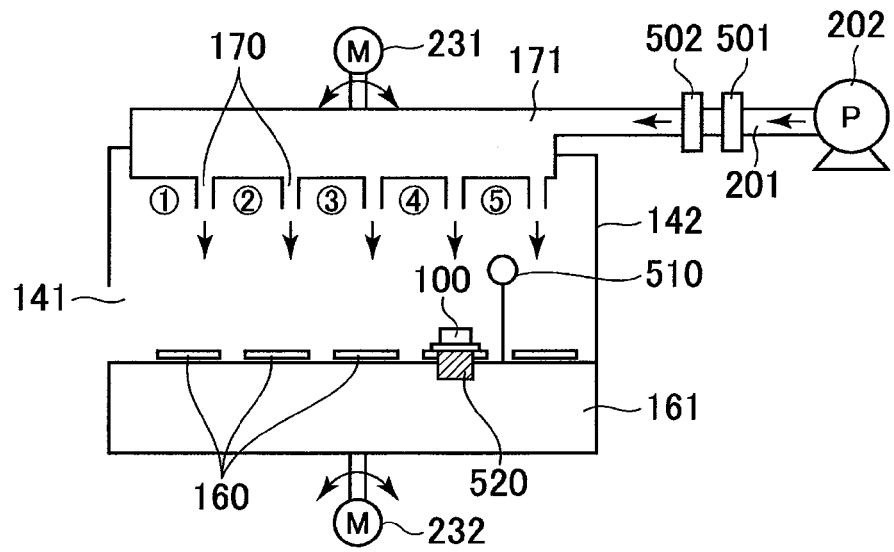
FIG. 6 is a schematic diagram of an incubator unit in an embodiment of the present invention.

FIG. 6 is an explanatory drawing schematically showing the setup inside an incubator unit similarly to FIG. 3. A heater 501 and a humidifier 502 are provided in the middle of the pipe 201 connecting the air pump 202 to the nozzle disk 171, with which the temperature and humidity in the incubator are kept constant. A temperature sensor 510 is placed in midair inside the incubator at a position between two reaction container setting spots 160 so as not to obstruct the stirring operation. The temperature sensor 510 monitors the temperature inside the incubator during the stirring operation.

Figure 7:
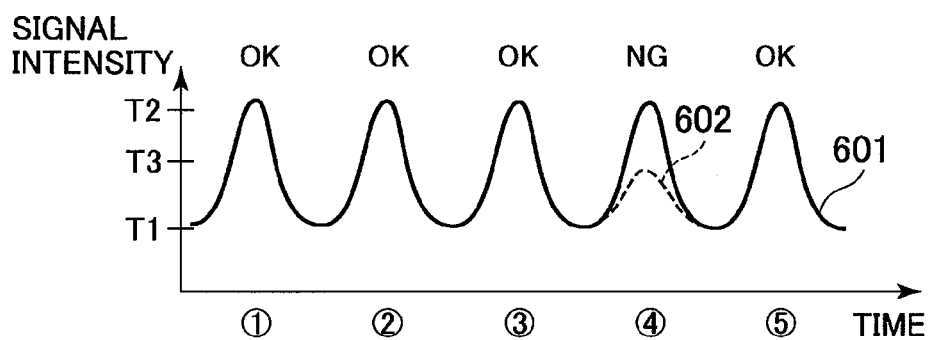
FIG. 7 shows an example of the output of temperature detecting means in the embodiment of the present invention.

In the initialization operation before or after the stirring operation, if the nozzle disk 171 is rotated while the compressed air is ejected from all the nozzles 170, the jets of the compressed air ejected from the nozzles 170 successively pass over the temperature sensor 510. FIG. 7 shows an example of the output value of the temperature sensor 510 in this case, wherein the horizontal axis represents time and the vertical axis represents the output value. The output value repeats increasing and decreasing at fixed periods in response to the passage of the nozzles #1-#5. Even when the inside of the incubator unit 140 is kept at a temperature T1, the temperature of the compressed air just after being ejected from the nozzle is higher than T1 since the compressed air has just been heated by the heater. Therefore, the output value of the temperature sensor 510 repeats increasing and decreasing in a fixed pattern between the minimum value T1 and a maximum value T2 as indicated by the solid line 601 if the nozzles are in their normal states. However, if an abnormality such as the displacement or the clogging (due to adhesion of dust) has occurred to the nozzle #4, for example, as explained in the previous embodiment referring to FIG. 4, the increase/decrease pattern changes (e.g., the maximum value decreases to T3) as indicated by the broken line 602. The nozzle abnormality can be detected by comparing the change (changed value) with the normal value. Incidentally, equivalent effects can be achieved by using a humidity sensor instead of the temperature sensor. It is possible to provide a plurality of sensors similarly to the first embodiment, which is desirable since the amount of acquirable information increases. It is also possible to provide a sensor at every interval between adjoining reaction container setting spots 160, which is more desirable since the amount of acquirable information increases further.

Figure 8:
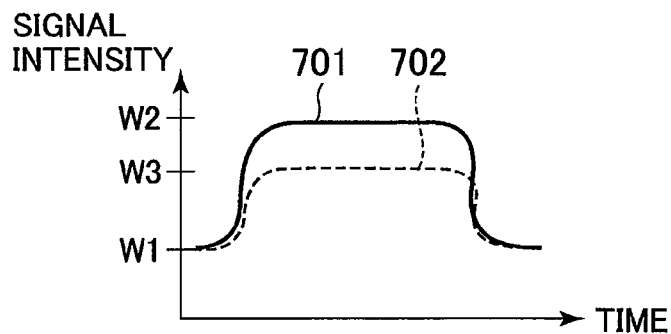
FIG. 8 shows an example of the output of a load sensor in the embodiment of the present invention.

Meanwhile, one of the reaction container setting spots 160 is equipped with a load sensor 520 as shown in FIG. 6 so that the load on the reaction container 100 set on the reaction container setting spot 160 can be detected. The reaction container 100 receives force when the compressed air is applied to the reaction solution during the stirring operation. FIG. 8 shows an example of a graph representing the output of the load sensor 520, wherein the horizontal axis represents time and the vertical axis represents the load sensor output. When the nozzle above the load sensor is in the normal state, the output value of the load sensor changes between a minimum value W1 and a maximum value W2 as indicated with the solid line 701. When the displacement or the clogging with adhering dust has occurred to the nozzle as shown in FIG. 4, the increase/decrease pattern changes (e.g., the maximum value decreases to W3) as indicated with the broken line 702. Therefore, the nozzle abnormality can be detected in the midst of the stirring operation. Incidentally, while only one reaction container setting spot 160 is equipped with the load sensor 520 in this embodiment, it is possible to equip every reaction container setting spot 160 with the load sensor 520. Such a configuration is desirable since the stirring status of all the reaction containers 100 can be monitored.

Third Embodiment

Figure 9:
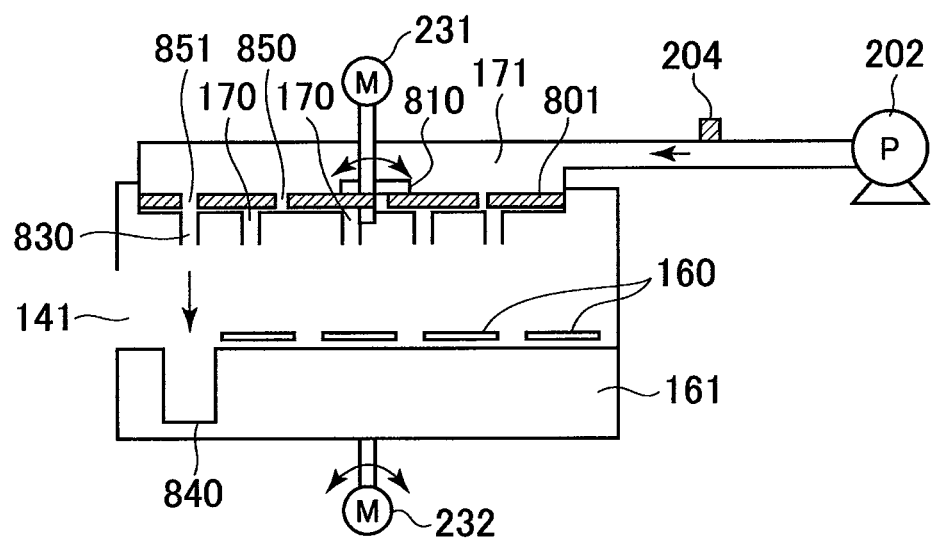
FIG. 9 is a schematic diagram of an incubator unit in an embodiment of the present invention.

FIG. 9 is an explanatory drawing schematically showing the setup inside an incubator unit similarly to FIG. 3. A flushing disk 801 is provided in a part of the nozzle disk 171 close to the nozzles 170. The connection between the flushing disk 801 and the nozzle disk 171 can be switched by a key groove mechanism 810. By the switching, the flushing disk 801 can either be driven together with the nozzle disk 171 by the drive motor 231 or be separated from the nozzle disk 171 and fixed inside the incubator.

Figure 10:
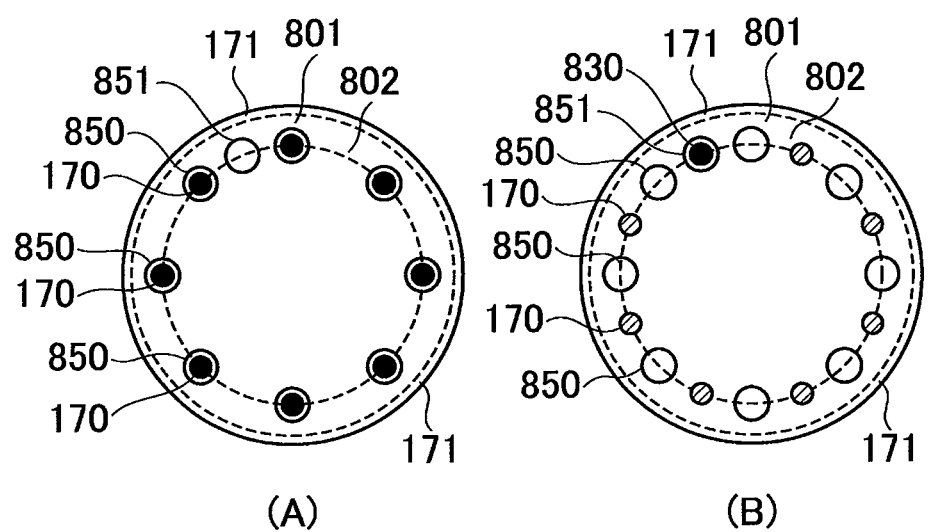
FIG. 10(A) is a schematic diagram showing arrangements of a nozzle disk and a flushing disk during a stirring operation in the embodiment of the present invention.
FIG. 10(B) is a schematic diagram showing arrangements of a nozzle disk and a flushing disk during a flushing operation in the embodiment of the present invention.

FIG. 10 shows the positional relationship among the nozzle disk 171, the nozzles 170, the flushing disk 801, etc. viewed from the reaction disk 161, wherein FIG. 10(A) shows the positional relationship during the stirring operation and FIG. 10(B) shows the positional relationship during a flushing operation. The flushing disk 801 is a component in a disk-like shape, having a flushing through hole 851 and a plurality of stirring through holes 850 formed on the same circumference 802. In the stirring operation, the flushing disk 801 and the nozzle disk 171 rotate together. The compressed air to be ejected from the nozzles 170 passes through the stirring through holes 850 (formed at positions corresponding to the nozzles) to stir the reaction solutions.

In the initialization operation, the flushing of the nozzles (removal of dust, etc. adhering to the nozzles) is carried out by letting a large amount of air flow through the nozzles. In the flushing operation, only the nozzle disk 171 is rotated while fixing the flushing disk 801 in the incubator. As shown in FIG. 9 and FIG. 10(B), the compressed air is ejected from only one nozzle 830 via the flushing through hole 851, while the other nozzles 170 are capped by the flushing disk 801 serving as strong fluid resistance. Therefore, even without the need of a high flow setting of the air pump 202, the flushing can be conducted successfully since a large amount of air flows exclusively through the nozzle 830 connected with the flushing through hole 851. The flushing can be conducted to all the nozzles since all the nozzles pass through the flushing through hole 851 along with the rotation of the nozzle disk 171.

In a part of the reaction disk 161 under the flushing through hole 851, a deep hole 840 is formed so that the removed dust from the nozzles can be stored therein.

During the flushing operation, the output of the pipe pressure sensor 204 is monitored. The monitoring makes it possible to check whether the dust, etc. has been removed successfully from the nozzle 830 or not since the output value increases when the clogging, etc. has occurred to the nozzle 830 and returns to a certain level upon the removal of the dust, etc.

With the above configuration and operation, the clogging of the nozzles can be eliminated. This embodiment implements the flushing of the nozzles at a lower cost in comparison with cases where a large amount of air is let through all the nozzles at once by use of a high flow pump. This embodiment implements the flushing at a lower cost also in comparison with cases where each nozzle is equipped with a valve as a means to block up each nozzle other than the nozzle 830.

Fourth Embodiment

Figure 11:
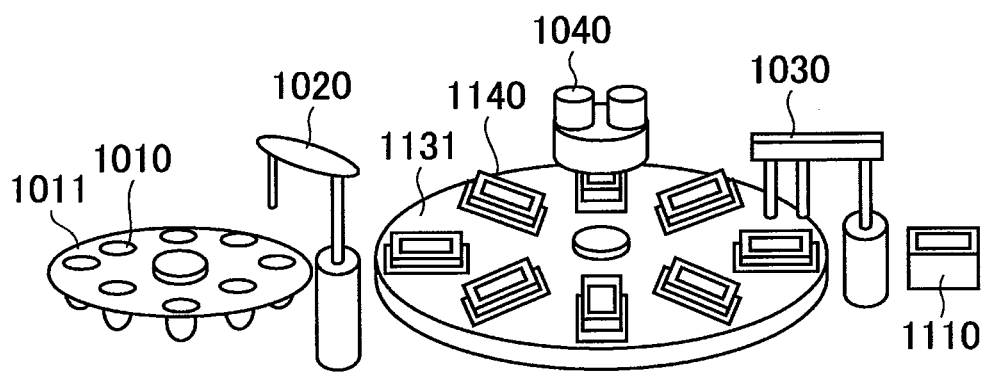
FIG. 11 is an overall schematic diagram of a chemical analyzer in accordance with an embodiment of the present invention.

FIG. 11 is an overall schematic diagram of a chemical analyzer in accordance with a forth embodiment of the present invention. The chemical analyzer comprises a sample disk 1011 for storing sample containers 1010, a reaction disk 1131 on which small-sized reaction containers 1140 are set, a separate pouring mechanism 1020 for pouring samples separately to the reaction containers, a washing mechanism 1030 for washing the reaction containers, a washing bath 1110 for washing the washing mechanism, and an optical detection mechanism 1040 including an excitation light irradiator and a fluorescence emission intensity detector. The reaction disk 1131 is a component in a disk-like shape, having the plurality of reaction containers 1140 provided along its circumference. These components operate automatically with prescribed timing as explained below based on previously inputted analysis item information. First, a sample is separately poured from the sample container 1010 to the reaction container 1140 by the separate pouring mechanism 1020. Then, a chemical reaction starts in a reaction region at the bottom of the reaction container. The reaction container in which the chemical reaction has completed is moved to a prescribed position nearby the washing mechanism 1030 by the rotation of the reaction disk 1131. At the position, the washing mechanism 1030 descends to the reaction container and washes the reaction container. The reaction container after being washed is moved to a position under the detection mechanism 1040 by the rotation of the reaction disk 1131. At the position, the result of the reaction in the reaction region is detected by the detection mechanism 1040.

Figure 12:
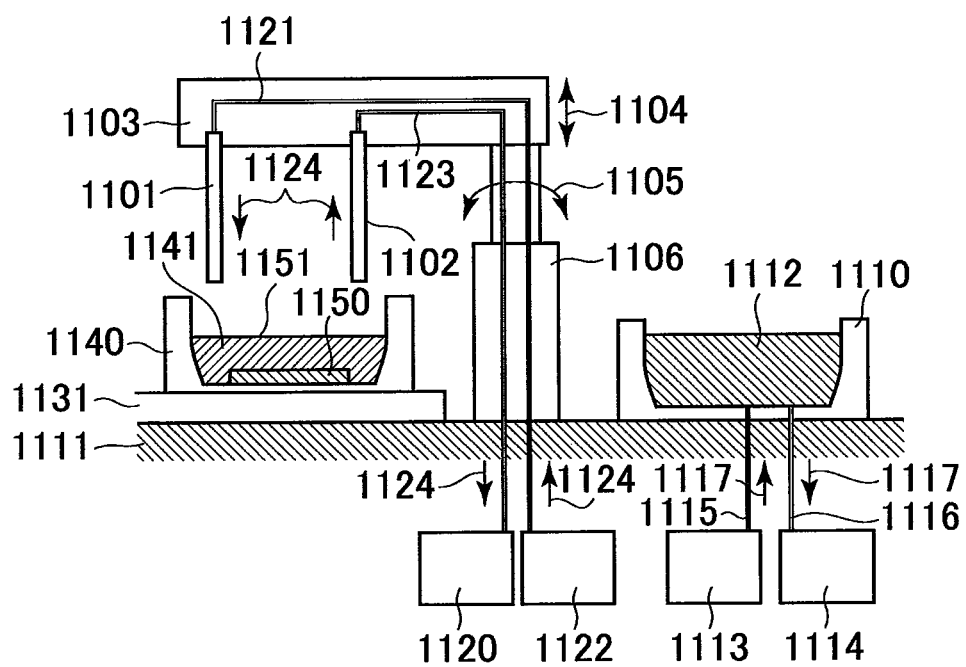
FIG. 12 is a schematic diagram of a washing mechanism in the embodiment of the present invention.

FIG. 12 is a schematic diagram of the washing mechanism. The washing mechanism includes a washing head operation mechanism 1106 and the washing bath 1110 provided on the base 1111 of the analyzer. The washing head operation mechanism 1106 vertically moves and horizontally rotates a washing head 1103, having a discharge pipe 1101 and a suction pipe 1102 for the discharge and the suction of a cleaning fluid, as indicated by the arrows 1104 and 1105. The washing bath 1110 is used for washing the tips of the discharge pipe and the suction pipe. A cleaning fluid feeding mechanism 1120, including a cleaning fluid tank and a discharge pump, is connected to the discharge pipe 1101 via piping 1121. Similarly, a cleaning fluid suction mechanism 1122, including a suction pump and a waste fluid tank, is connected to the cleaning fluid suction pipe 1102 via piping 1123. The arrows 1124 indicate the directions of the flow of the cleaning fluid. A washing pipe cleaning fluid feeding mechanism 1113 (including a cleaning fluid tank and a discharge pump for supplying and discarding a washing pipe cleaning fluid 1112) and a washing pipe waste fluid suction mechanism 1114 (including a waste fluid tank and a suction pump) are connected to the washing bath 1110 (for washing the tips of the discharge pipe 1101 and the suction pipe 1102) via piping 1115 and piping 1116, respectively. The arrows 1117 indicate the directions of the flow of the washing pipe cleaning fluid.

Figure 13:
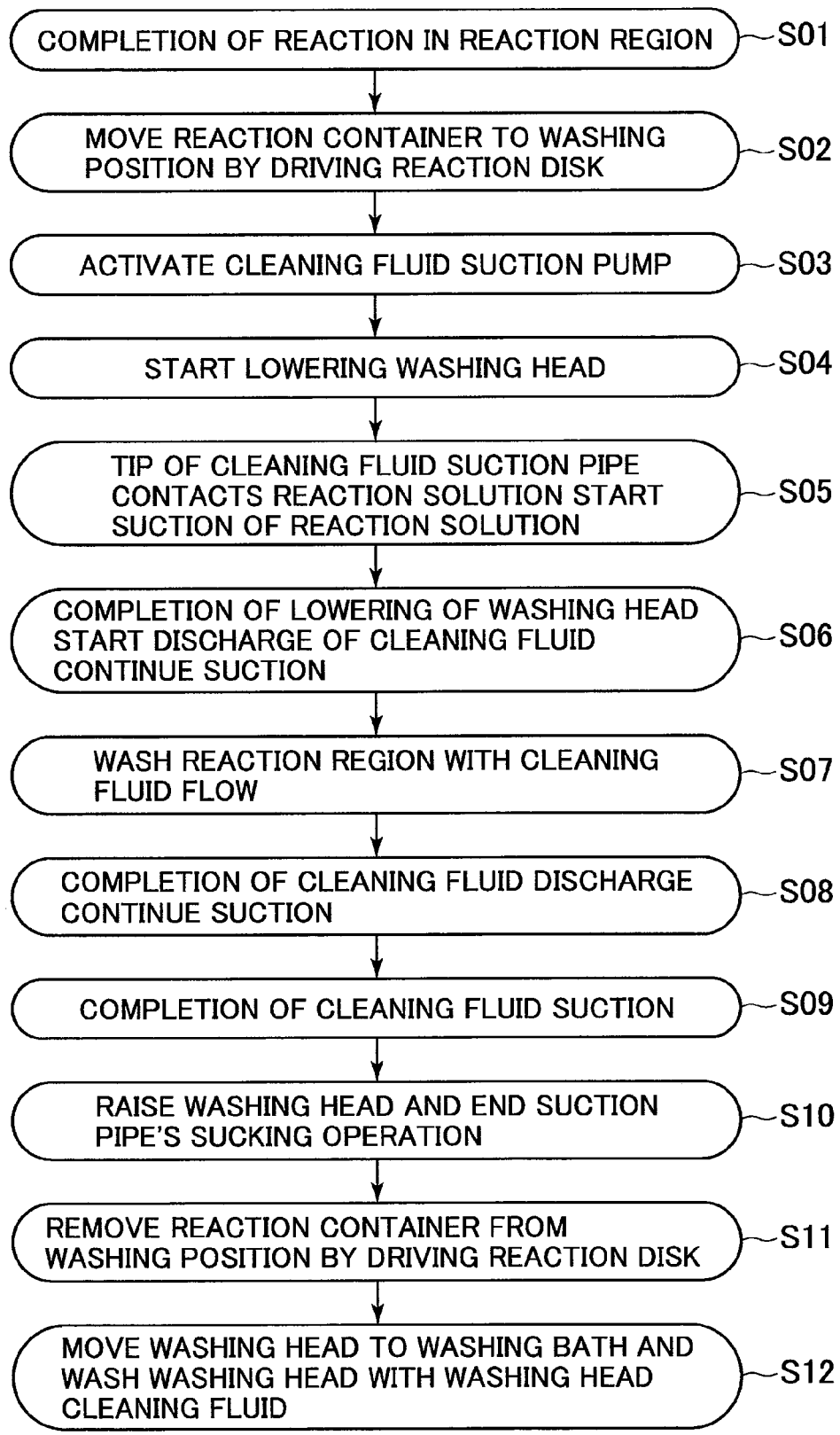
FIG. 13 is a flow chart of a washing operation in the embodiment of the present invention.

FIG. 13 is a flow chart of the washing operation. When the reaction in the reaction region is completed (S01 in FIG. 13), the reaction disk 1131 is rotated first, by which the reaction container 1140 is moved to the washing position (S02 in FIG. 13). Subsequently, the suction pump of the cleaning fluid suction mechanism 1122 is activated (S03 in FIG. 13) and the washing head 1103 is lowered with the suction pump ON (S04 in FIG. 13). Then, the suction of the reaction solution starts at the instant that the tip of the suction pipe 1102 contacts the surface 1151 of the reaction solution 1141 (S05 in FIG. 13). Since the cleaning fluid suction unit (suction pump) is already in operation as above, the reaction solution is discharged from the reaction container first, by which the cleaning efficiency is improved compared to cases where the cleaning fluid mixed with the reaction solution is circulated in the reaction container. Further, if the washing pipes are soaked in the reaction solution when the reaction container is full of the reaction solution, the reaction solution may overflow from the reaction container, contaminate the analyzer, and deteriorate the reliability of the analyzer. This embodiment eliminates such a problem since the reaction solution has sufficiently been discharged from the reaction container at the point when the lowering of the washing head is completed. After the lowering of the washing head 1103 is completed, discharge of the cleaning fluid from the discharge pipe 1101 is started while continuing the suction through the suction pipe 1102 (S06 and S07 in FIG. 13).

Figure 14:
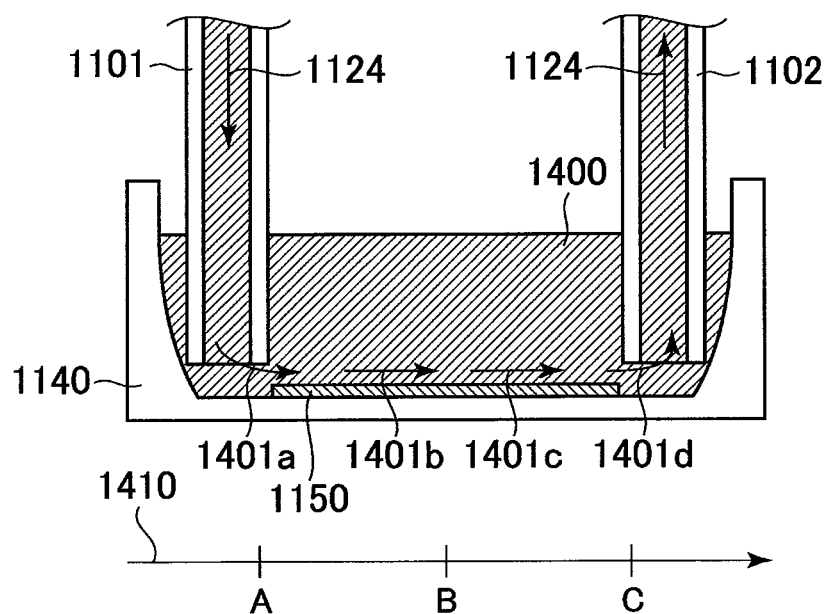
FIG. 14 is a schematic diagram showing central cross sections of a reaction container, a discharge pipe and a suction pipe for explaining the washing of the reaction container in the embodiment of the present invention.

FIG. 14 is a schematic diagram showing central cross sections of the reaction container, the discharge pipe and the suction pipe for explaining the washing of the reaction container at this stage. In FIG. 14, the axis 1410 indicates positions on the central axis of the reaction container, the reference characters A and C represent both ends of the reaction region 1150, and the reference character B represents the center of the reaction region. The discharge pipe 1101 and the suction pipe 1102 are placed as close to the side wall of the reaction container 1140 as possible so that the pipes 1101 and 1102 do not interfere with the reaction region 1150. In this state, the cleaning fluid 1400 is discharged from the discharge pipe 1101 and sucked by the suction pipe 1102 as indicated by the arrows 1124, by which a cleaning fluid flow indicated by the arrows 1401a, 1401b, 1401c and 1401d is formed in the reaction region 1150. As above, the suction of the cleaning fluid is carried out not after filling the reaction container with the cleaning fluid but concurrently with the discharge of the cleaning fluid from the discharge pipe 1101. This constantly forms the cleaning fluid flow at the bottom of the reaction container during the washing operation, by which the reaction region can be washed and cleaned sufficiently.

Figure 19:
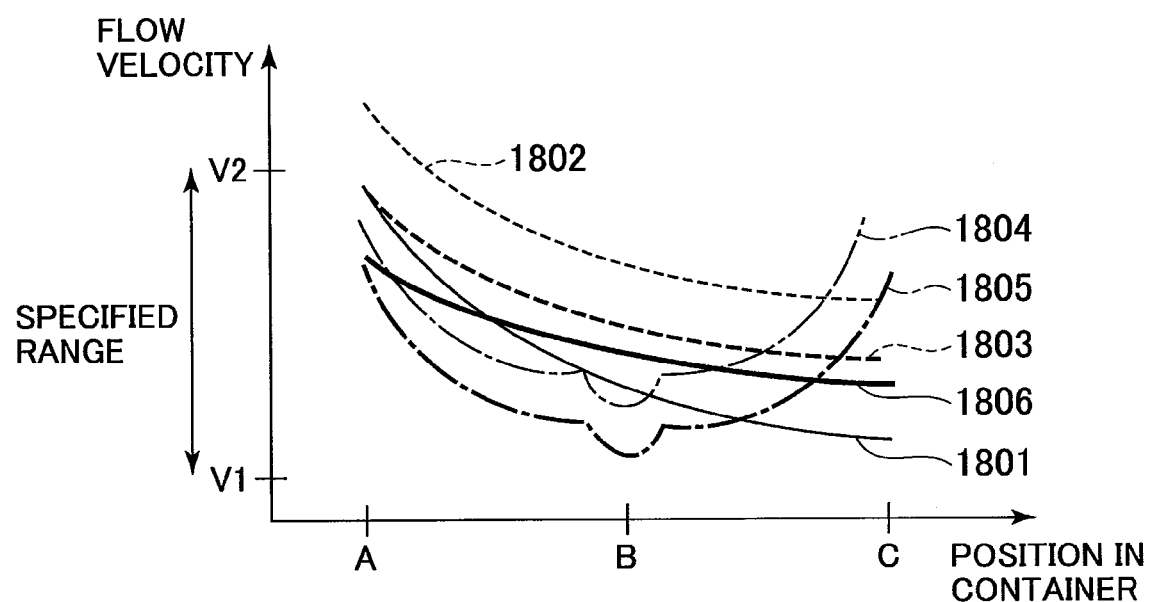
FIG. 19 shows flow velocity distribution on the central cross section of the reaction container in the washing operation in embodiments of the present invention.

FIG. 19 shows an example of flow velocity distribution of the cleaning fluid flow on the central axis of the bottom of the reaction container, wherein the horizontal axis represents the position in the reaction container and the vertical axis represents the flow velocity. A flow velocity range not harming the reaction region is between V1 and V2. Flow velocity lower than V1 lead to insufficient washing, while flow velocity higher than V2 cause exfoliation in the reaction region. The flow velocity distribution in this embodiment is indicated with a solid line 1801 in FIG. 19. The flow velocity 1401*a* under the discharge pipe 1101 is high since the cross-sectional area of the channel for the cleaning fluid formed between the tip of the discharge pipe and the bottom of the reaction container is small. However, the cleaning fluid flow does not harm the reaction region since the maximum flow velocity does not exceed V2 as indicated by the solid line 1801 in FIG. 19. Meanwhile, the flow velocity does not fall below V1 even at the minimum point B. Therefore, the reaction region can be washed and cleaned sufficiently. Incidentally, while the flow velocity distribution on the central axis is shown in FIG. 19, the flow velocity distribution has been confirmed to be within the above flow velocity range throughout the bottom of the reaction container (the same goes for the following embodiments).

Even after the discharge of a prescribed amount of cleaning fluid is finished and the washing of the reaction region is completed, the sucking operation is continued (S08, S09 and S10 in FIG. 13), by which the cleaning fluid is totally sucked out of the reaction container. If some of the cleaning fluid remains in the reaction container, optical reflection may occur on the surface of the remaining fluid and that deteriorate the detection accuracy. Such a problem can be prevented by the continuation of the sucking operation.

Thereafter, the washing head 1103 is raised, the sucking operation is ended, and the reaction container 1140 is removed from the washing position by rotating the reaction disk 1131 (S10, S11 and S12 in FIG. 13). Meanwhile, the tips of the discharge pipe 1101 and the suction pipe 1102 are inserted into the washing bath 1110 by rotating and lowering the washing head 1103, the tips of the pipes 1101 and 1102 are washed with the washing pipe cleaning fluid 1112 circulated in the washing bath, and the whole washing operation is finished (S12 in FIG. 13).

Fifth Embodiment

Figure 15:
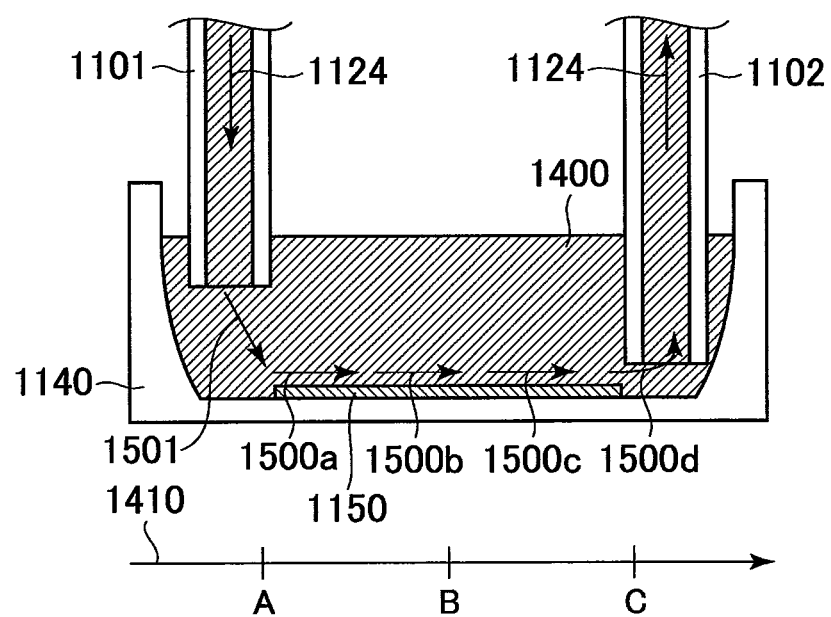
FIG. 15 is a schematic diagram showing central cross sections of a reaction container, a discharge pipe and a suction pipe for explaining the washing of the reaction container in an embodiment of the present invention.

Another embodiment will be described below. FIG. 15 is a schematic diagram showing the central cross sections of the reaction container, a discharge pipe and a suction pipe in the washing operation similarly to FIG. 14. In this embodiment, the tip of the suction pipe is placed closer to the bottom of the reaction container compared to the tip of the discharge pipe. The position of the tip of the discharge pipe is desired to be not higher than the opening of the reaction container as shown in FIG. 15 so that the cleaning fluid does not scatter around during the washing.

The washing operation is performed as shown in FIG. 13. As the washing head 1103 shown in FIG. 12 is lowered, only the tip of the suction pipe 1102 makes contact with the reaction solution surface 1151 and the suction of the reaction solution 1141 starts (S04 and S05 in FIG. 13). If the tips of the discharge pipe 1101 and the suction pipe 1102 are at the same height, the tip of the discharge pipe 1101 also makes contact with the reaction solution 1141 and is contaminated with the reaction solution. Such a problem can be avoided by this embodiment.

When the lowering of the washing head is completed and the discharge of the cleaning fluid is started (S06 and S07 in FIG. 13), a flow of the cleaning fluid 1400 occurs at the bottom of the reaction container 1140 as indicated with the arrows 1500*a*, 1500*b*, 1500*c* and 1500*d* in FIG. 15.

If the amount of flow is increased in the fourth embodiment, the flow velocity distribution changes to that indicated with the dotted line 1802 in FIG. 19 and the flow velocity at the point A increases to V3 higher than V2. However, in the case of FIG. 15 where the tip of the discharge pipe is far apart from the bottom of the reaction container, the velocity of the flow 1500*a* is low since the flow 1501 from the discharge pipe is gradually decelerated by friction with surrounding cleaning fluid. In this case, the maximum velocity decreases and the flow velocity distribution fits in the range between V1 and V2 as indicated with the thick dotted line 1803 in FIG. 19. Thus, the reaction container can be washed and cleaned sufficiently without harming the reaction region.

Subsequently, the discharge of the cleaning fluid is finished and only the suction is continued (S08 and S09 in FIG. 13). If the tip of the discharge pipe is situated close to the bottom of the reaction container at this stage, some cleaning fluid tends to remain in the reaction region in spite of the suction due to adhesion to the part around the tip of the discharge pipe. In this embodiment, the discharge pipe is far apart from the bottom, and thus the problem (cleaning fluid left in the reaction region) can substantially be eliminated, contributing to the securement of high analysis accuracy.

Sixth Embodiment

Figure 16:
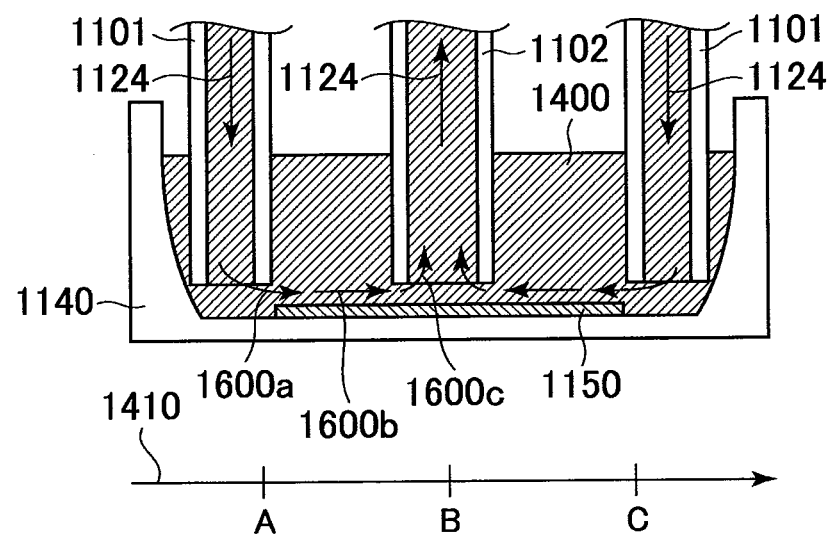
FIG. 16 is a schematic diagram showing central cross sections of a reaction container, discharge pipes and a suction pipe for explaining the washing of the reaction container in an embodiment of the present invention.

Still another embodiment will be described below referring to FIGS. 12, 13 and 16. FIG. 16 is a schematic diagram showing the central cross sections of the reaction container, discharge pipes and a suction pipe in the washing operation similarly to FIG. 14.

In this embodiment, two discharge pipes and one suction pipe are used. The discharge pipes 1101 are placed at both ends of the reaction region 1150, while the suction pipe 1102 is placed at the center of the reaction region 1150.

The washing operation is performed as shown in FIG. 13. When the lowering of the washing head 1103 shown in FIG. 12 is completed and the discharge of the cleaning fluid is started (S06 and S07 in FIG. 13), a flow of the cleaning fluid 1400 occurs at the bottom of the reaction container as indicated with the arrows 1600*a*, 1600*b* and 1600*c* in FIG. 16. The flow velocity distribution at this stage is indicated with a chain line 1804 in FIG. 19. In this embodiment, however, the cleaning flow velocity is high even at the point B since the flow path of the cleaning fluid flow 1600*a*, 1600*b*, 1600*c* is shorter than that in the cases where the discharge pipe and the suction pipe are placed at the ends of the reaction region (e.g., embodiments 4 and 5). Even though the flow velocity drops at some points since the point B is like a stagnation point where discharge flows from both sides collide with each other, the flow velocity distribution fits in the range between V1 and V2. Thus, the reaction container can be washed and cleaned sufficiently without harming the reaction region. Conversely, by taking advantage of this relationship, it is possible to reduce the running cost by decreasing the amount of flow, that is, decreasing the amount of the cleaning fluid used for the washing. The flow velocity distribution in this case is indicated with a thick chain line 1805 in FIG. 19. Even though the maximum value has dropped to V5, the flow velocity distribution is still within the range between V1 and V2. Thus, the reaction container can be washed and cleaned sufficiently without harming the reaction region.

Seventh Embodiment

Figure 17:
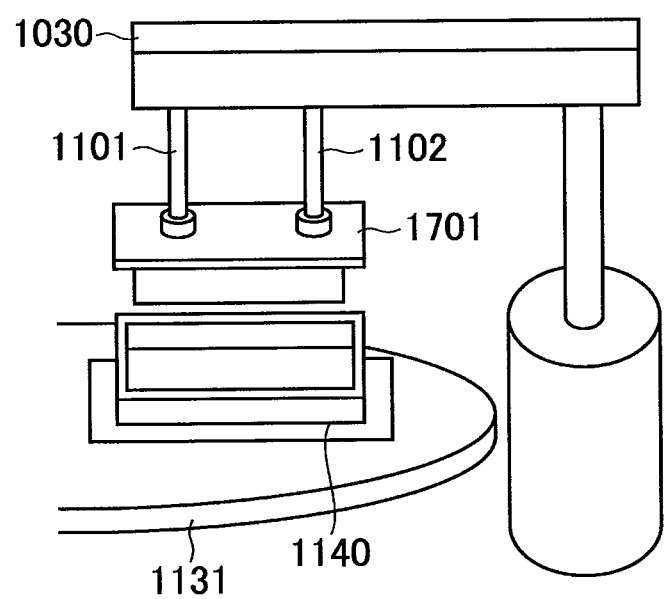
FIG. 17 is an enlarged view of a washing position shown in FIG. 11.
Figure 18:
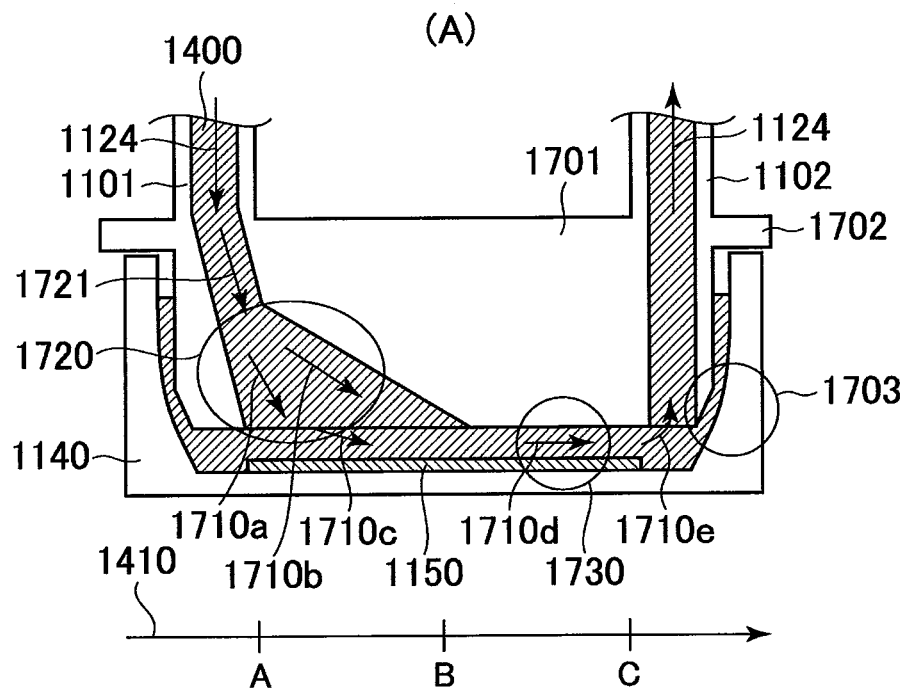
Figure 18:
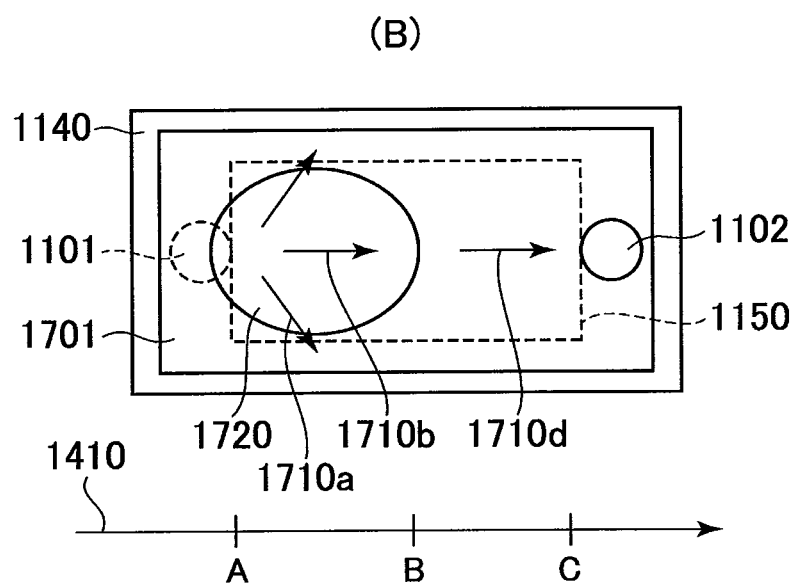

Still another embodiment will be described below referring to FIGS. 12, 13, 17 and 18. FIG. 17 is an enlarged view of the washing position shown in FIG. 11. FIG. 18 is a schematic diagram for explaining the reaction container, a cleaning fluid discharge pipe, a suction pipe, a rinse chip and the cleaning fluid flow in the washing operation, wherein FIG. 18(A) is a central cross-sectional view and FIG. 18(B) is a bottom view of the reaction container. In this embodiment, a structure called "rinse chip 1701", serving as the top of the reaction container 1140, is attached to the tips of the discharge pipe 1101 and the suction pipe 1102 as shown in FIG. 17.

The washing operation is performed as shown in FIG. 13. The cleaning fluid suction unit (suction pump) of the cleaning fluid suction mechanism 1122 shown in FIG. 12 is activated (S03 in FIG. 13) and the washing head 1103 is lowered into the reaction container 1140 with the suction pump ON (S04 in FIG. 13). Then, the suction of the reaction solution starts at the instant that the tip of the rinse chip 1701 contacts the surface 1151 of the reaction solution 1141 (S05 in FIG. 13). Since the cleaning fluid suction unit is already in operation as above, the reaction solution is discharged from the reaction container first, by which the cleaning efficiency is improved compared to cases where the cleaning fluid mixed with the reaction solution is circulated in the reaction container. Further, if the rinse chip is soaked in the reaction solution when the reaction container is full of the reaction solution, the reaction solution may overflow from the reaction container, contaminate the analyzer, and deteriorate the reliability of the analyzer. This embodiment eliminates such a problem since the reaction solution has sufficiently been discharged from the reaction container at the point when the lowering of the washing head is completed.

In order to prevent the base of the rinse chip 1701 from contacting the reaction region 1150 when the lowering of the washing head 1103 is completed (S06 in FIG. 13), a latch 1702 for positioning the rinse chip 1701 by contacting the top of the reaction container 1140 is desired to be formed in the upper part of the rinse chip 1701. The latch 1702, which covers and stops up the opening of the reaction container 1140, also prevents the reaction solution and the cleaning fluid from overflowing from the reaction container 1140 during the washing operation. The side face 1703 of the rinse chip is desired to be cut in a shape like that of the side wall of the reaction container 1140 so that the base of the rinse chip 1701 can get close to the bottom of the reaction container 1140.

When the discharge of the cleaning fluid is started (S06 and S07 in FIG. 13), a flow of the cleaning fluid 1400 occurs at the bottom of the reaction container as indicated with the arrows 1710a, 1710b, 1710c, 1710d and 1710e in FIG. 18. When only the discharge pipe and the suction pipe are used as in the fourth through sixth embodiments, it is difficult to define the flow path of the cleaning fluid since the surface of the cleaning fluid can move freely. Consequently, the control of the flow velocity of the cleaning fluid is difficult. In contrast, by using the rinse chip as in this embodiment, the flow path of the cleaning fluid flow can structurally be defined between the rinse chip and the bottom of the reaction container. This makes it possible to reduce the amount of the cleaning fluid used for the washing, which contributes to the reduction of the running cost. Incidentally, if a broadening flow path 1720 is formed on the discharge pipe's side as shown in FIG. 18(A), the flow velocity of the cleaning fluid becomes high in the discharge flow 1721 and low in the downstream flows 1710a, 1710b and 1710c. On the suction pipe's side, the flow velocity is high in the flows 1710d and 1710e since a flow channel 1730 with a small cross-sectional area is formed between the rinse chip 1701 and the bottom of the reaction container 1140. The flow velocity distribution in this case is indicated with a thick solid line 1806 in FIG. 19.

In comparison with the solid line 1801, even though the maximum flow velocity decreased due to the reduction of the amount of flow, the flow velocity increased at the points B and C. Therefore, the reaction container can be washed and cleaned sufficiently without harming the reaction region.

In the case where the rinse chip is attached to the tips of the washing pipes, the rinse chip, which is larger than the tips of the washing pipes, is immersed in the reaction solution, and thus the cleaning of the washing head has to be conducted sufficiently in order to prevent the contamination. In this case, the rinse chip is desired to be formed of water-repellent material such as polyethylene terephthalate.

Figure 20:
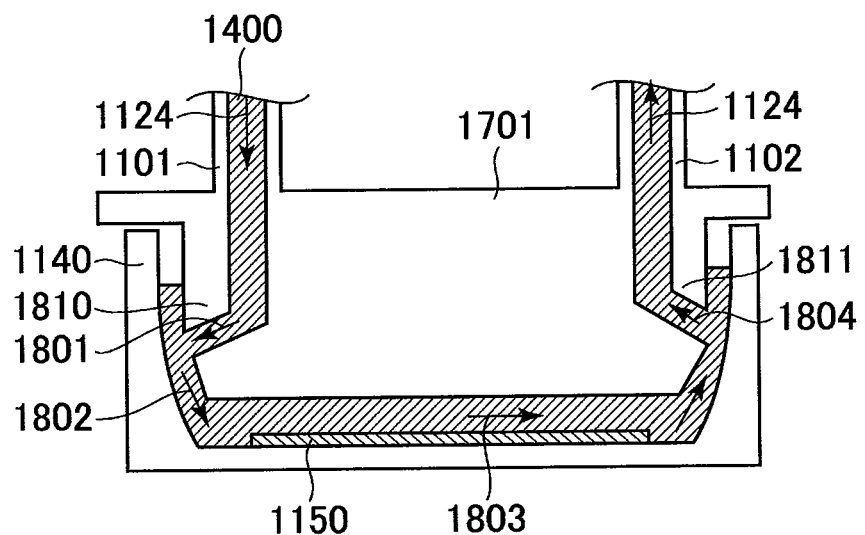
Figure 20:
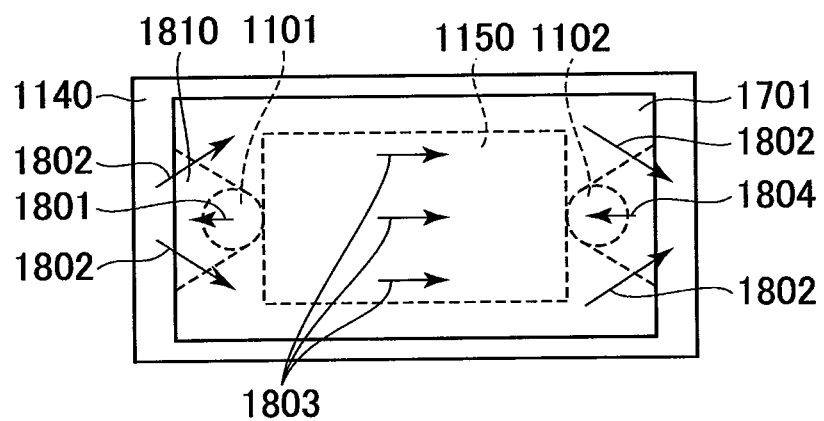

A rinse chip of a lateral channel type may also be employed as shown in FIG. 20.

In the example of FIG. 20, lateral channels 1810 and 1811, extending laterally from the discharge pipe 1101 and the suction pipe 1102, are formed in the rinse chip 1701. Thanks to the lateral channel 1810, the fluid discharged from the discharge pipe forms a flow 1801 that does not directly collide with the bottom of the reaction container, by which damage to the coating reagent 1150 is reduced and the detection accuracy is improved. Further, since the lateral channel 1810 is formed in a shape broadening toward the microchip base, the cleaning fluid flows from the side to the microchip base uniformly like the cleaning fluid flows 1802 and 1803, which improves the washing efficiency. Also in the suction, the cleaning fluid is sucked by the lateral channel 1811 in a contracting flow (e.g., cleaning fluid flow 1802). Consequently, a uniform flow field is formed and the washing efficiency is improved.

DESCRIPTION OF REFERENCE CHARACTERS

100 reaction container
161 reaction disk
nozzle
nozzle disk

The invention claimed is:
1. A chemical analyzer comprising:
a reaction container setting table on which a plurality of reaction containers, each having an opening thereon are set;
a pipetting mechanism for pouring a sample and a reagent separately from their respective containers to ones of the reaction containers;
an air ejection hole for ejecting air to one of the reaction containers from above the reaction container setting table so as to stir and mix the sample and the reagent in the one of the reaction containers;
a detection mechanism for detecting a result of a reaction of the sample and the reagent in the one of the reaction containers;
a driving motor for moving the air ejection hole or the reaction container setting table to change a positional relationship between the air ejection hole and the reaction container setting table;
at least one pressure sensor which is disposed within the reaction container setting table so as to sense pressure via a pore formed through the reaction container setting table, wherein the at least one pressure sensor continuously detects pressure changes of the air ejected from the air ejection hole while a positional relationship between the air ejection hole and the at least one pressure sensor is changed by the driving mechanism; and a controller that compares a pressure measurement value detected by the at least one pressure sensor with a preset pressure threshold value and reports an occurrence of a preset difference between the measurement value and the preset threshold value when the occurrence of the preset difference between the measurement value and the preset threshold value is detected.

2. The chemical analyzer according to claim 1, further comprising:

an incubator in which the reaction container setting table and the air election hole are installed, wherein the air ejection hole faces downward and is disposed at an upper part of the incubator.

3. The chemical analyzer according to claim 1, further comprising:

a flushing disk which eliminates clogging of the air ejection hole.

* * * * *